United States Patent [19]

van Andel

[11] Patent Number: Plant 5,544

[45] Date of Patent: Aug. 27, 1985

[54] CARNATION NAMED STANQUIN

[75] Inventor: Jacob van Andel, Aalsmeer, Netherlands

[73] Assignee: B. V. Handelskwekerij M. C. van Staaveren, Aalsmeer, Netherlands

[21] Appl. No.: 556,261

[22] Filed: Nov. 30, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of carnation plant distinguished by the very light chartreuse-green coloring of its medium sized blooms which are borne raceme on long, strong flower stems, by its upright growth habit with good strength and continuous Spring and Fall flower production.

1 Drawing Figure

BACKGROUND OF THE NEW PLANT

This new carnation plant originated as a seedling produced by my crossing of selected unnamed varieties at Aalsmeer, Holland, with the object of developing plants having new color, better production and resistance to *Fusarium oxysporum.* This plant was selected for propagation because of its bright light green-yellow coloration and the medium size of its flowers in which the flower petals are held together tightly to form a generally flat button-like appearance and propagation of this plant at Aalsmeer through successive generations has demonstrated that its distinguishing characteristics hold true from generation to generation and appear to be firmly fixed.

DESCRIPTION OF THE DRAWING

My new carnation cultivar is illustrated by the accompanying photographic drawing which shows several flower stems of the plant, including buds in various stages of formation and of opening, one of which has been hand painted to show the true color obtained by conventional professional photographic procedures.

DESCRIPTION OF THE NEW PLANT

The following is a detailed description of my new carnation cultivar based upon observation of plants grown under conventional greenhouse procedures at Aalsmeer, Holland, the color designations being according to The R.H.S. Colour Chart of The Royal Horticultural Society of London, England.

THE PLANT

Origin: Seedling.

Parentage:

*Seed parent.*—Unnamed Plant No. 7905-1D.

*Pollen parent.*—Unnamed Plant No. 7981-2D. These plants are unpatented spray carnations selected by me from plants maintained in greenhouse for breeding purposes at Aalsmeer, Holland, and identified in my records by the stated numbers.

Classification:

*Botanic.—Dianthus caryophyllus.*

*Commercial.*—Greenhouse carnation.

Form: Tall bush.

Growth: Vigorous and upright with good strength.

Branching: Normal.

Foliage:

*Quantity.*—Medium.

*Number of leaves.*—Depending on season.

*Size of leaf.*—Medium.

*Shape.*—Oblong.

*Texture.*—Smooth.

*Color.*—Upper side — Blue/Green with waxy layer. Under side — Blue/Green with waxy layer.

THE BUD

Size: Medium.

*Diameter.*—About 10 mm.

*Length.*—About 30 mm.

Form: Ovoid and pointed becoming generally cylindrical with rounded and pointed apex until sepals begin to divide.

Color of petals:

*When sepals first divide.*—R.H.S. 154C.

*When petals begin to unfurl.*—Green-yellow R.H.S. 1C-154C.

Sepals: Stand up as flower opens and curl back when flower is fully opened.

*Color.*—Inside and outside — Grey/Green.

Calyx:

*Shape.*—Funnel-shaped.

*Size.*—Medium.

*Splitting.*—Very little.

THE FLOWER

Blooming habit: Continuous Spring and Fall.

Size of bloom: Medium.

*Diameter.*—About 50 mm.

*Depth.*—About 20 mm.

Borne: Raceme on strong flower stems.

Shape: Generally flat when bloom first opens becoming slightly domed when bloom matures.

Petalage:

*Number of petals.*—From about 30 to 40.

*Arrangement.*—Generally imbricated.

*Shape of petals.*—Fan shaped with dentate margins.

*Texture.*—Soft.

*Color.*—All petals: Top side and reverse side and during all seasons — R.H.S. Green-yellow 1C-154C.

Flower stem:

*Length.*—Depends upon season.

*Color.*—Dark Green.

*Character.*—Strong and upright.

Persistence: Petals hang on and dry.

Fragrance: Very weak.

Disease resistance: Resistant to *Fusarium oxysporum* as observed at Aalsmeer, Holland.

Lasting quality:

*On plant.*—About 14 days.

*As cut flower.*—About 10 days.

REPRODUCTIVE ORGANS

Stamens: Of small number.

*Anthers.*—Size: Small. Color: Cream.

*Pollen.*—There is no pollen.

Pistils:

*Number.*—One.

*Style: Color: Yellow Green.*

This new carnation variety somewhat resembles the variety "Stangella". However, it has different flowering habits and another flower color.

I claim:

1. A new and distinct carnation variety, substantially as herein shown and described, characterized by its continuous production of very light green-yellow flowers of medium size.

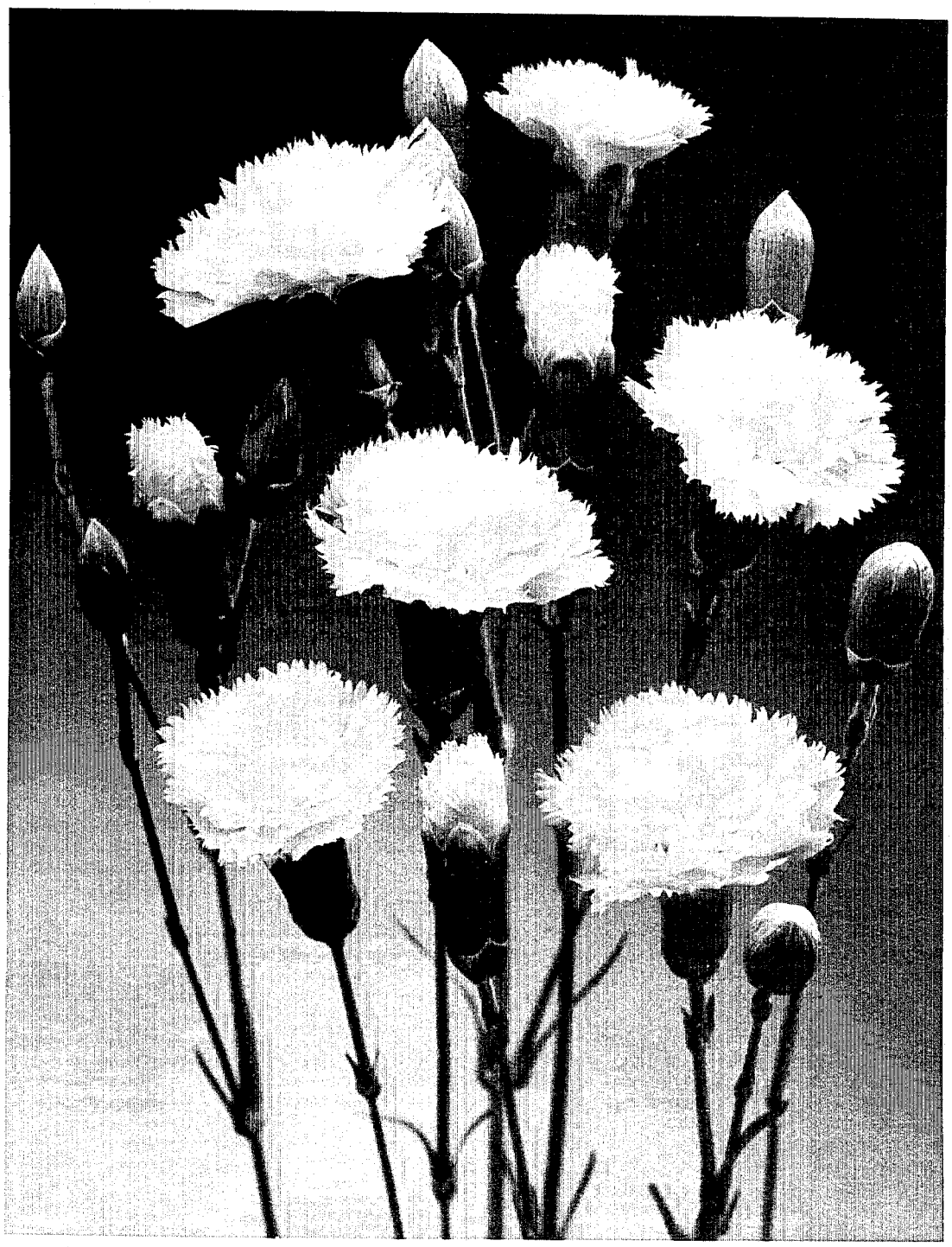

* * * * *